United States Patent [19]
Reger et al.

[11] Patent Number: 4,890,235
[45] Date of Patent: Dec. 26, 1989

[54] COMPUTER AIDED PRESCRIPTION OF SPECIALIZED SEATS FOR WHEELCHAIRS OR OTHER BODY SUPPORTS

[75] Inventors: Steven I. Reger, Shaker Heights; Donald C. Neth, Parma; Thomas F. McGovern, Cleveland Heights, all of Ohio

[73] Assignee: The Cleveland Clinic Foundation, Cleveland, Ohio

[21] Appl. No.: 219,606

[22] Filed: Jul. 14, 1988

[51] Int. Cl.$^4$ ............................................. G06F 15/46
[52] U.S. Cl. .................................... 364/468; 364/473; 364/413.01; 364/579; 297/458; 297/DIG. 4; 264/222; 264/313
[58] Field of Search ................... 364/468, 473, 413.01, 364/579; 297/458, DIG. 4; 264/222, 313-316

[56] References Cited

U.S. PATENT DOCUMENTS 4,637,789  1/1987  Netznik .............................. 264/316
4,828,325  5/1989  Brooks .............................. 297/458

OTHER PUBLICATIONS

S. I. Reger, et al., Computer Aided Prescription of Specialized Seats for Wheelchairs (Aug. 31, 1987).
S. I. Reger, et al., Shape and Pressure Distribution on Wheelchair Cushions, pp. 341-343 (9185).
S. I. Reger, et al., Instrumented, Adjustable Seat for Evaluating Posture and Body Contours, pp. 335-337 (1985).
D. A. Hobson, Research and Development Considerations and Engineering Perspective, pp. 122-129 (1986).
S. I. Reger, et al., Weightbearing Tissue Contour and Deformation by Magnetic Resonance Imaging, pp. 387-389 (1986).
G. W. McGrew, et al., Clinical Application of the Adjustable "Computer Chair", pp. 568-570 (1987).
K. C. Chung, et al., Comparative Evaluation of Pressure Distribution on Flat Foams, etc., pp. 323-325 (1987).
K. C. Chung, et al., Body Contours and Pressure Distributions of Normal and Sci Subjects, etc., pp. 515-517 (1987).
K. C. Chung, et al., Analysis of Compression, Shear and Surface Tension on Seat Cushions, pp. 269-271 (1987).
D. M. Brienza, et al., Design of a Computer Aided Manufacturing System for Custom Contoured Wheelchair Cushions, pp. 312-313 (1988).
K. C. Chung, et al., Effect of Contoured Support Surface on Pressure Distribution, pp. 314-315 (1988).
O. Nwaobi, et al. HIP Angle and Upper Extremity Movement Time in Children with Cerebral Palsy, pp. 39-41 (1985).

Primary Examiner—Allen MacDonald
Attorney, Agent, or Firm—Fay, Sharpe, Beall, Fagan, Minnich & McKee

[57] ABSTRACT

A system for generating a prescription wheelchair or other seating or body support arrangement includes a deformable seat portion. A patient to be fitted with the wheelchair is placed upon the seat deforming a surface thereof. A signal representative of force distribution resultant from the patient along the seat is generated. In accordance with this signal, the seat surface may be selectively varied by a plurality of pneumatic actuators. An updated force distribution signal is generated. In this fashion, a means and method is provided for arriving at preselected force distribution of the patient on the wheelchair seat. This data is made available for transmission to a fabrication unit from which a permanent seat cushion with the desired characteristics may be fabricated.

20 Claims, 3 Drawing Sheets

COMPUTER AIDED PRESCRIPTION OF SPECIALIZED SEATS FOR WHEELCHAIRS OR OTHER BODY SUPPORTS

BACKGROUND OF THE INVENTION

This application pertains to the art of specialized seating prescription, and more particularly to computer aided wheelchair seat design and fabrication.

The invention is particularly applicable to selective force distribution of a wheelchair patient by varying contour of a seat cushion, and will be described with particular reference thereto, although it will be appreciated that the invention has broader applications such as in fabrication of specialized beds, seating units, foot stools, or the like.

It is estimated that more than forty-five million people in the United States are affected by disabilities. There are nearly ten million of these individuals with limitation of activity that could benefit from application of rehabilitation engineering services. One common method used to overcome such a limitation of activity is implementation of wheelchairs. The number of daily wheelchair users exceeds 0.75 million people with a variety of disabilities.

An interface between a disabled individual and a wheelchair is crucial. Without an accurate fit of the interior support system, pressure sores and postural deformity results. Expenses for treatment of pressure sores and deformities are extremely high and are increasing. Estimates of the cost associated with the healing of pressure sores in 1978 were given to be between ten thousand dollars and forty-six thousand dollars. More recently, the range is shown to have widened to be from three thousand four hundred dollars to eighty-six thousand dollars with an increase of the mean cost of nearly ten thousand dollars.

More importantly, the gradual increase in spinal, pelvic, and femoral malalignment resulting from incorrect support can result in tissue break down, reduced functional capacity, increased dependence on attended care, diminished respiration, infection, and possible complications leading to death.

When chosen correctly, cushions and body supports can be effective in reducing the risk of pressure sores and maintaining postural alignment. The subject of wheelchair cushions is well documented in the literature. Various methods of selection, testing, as well as characteristics, have been described. Body support systems have been studied much less than seat cushions and are less defined in their use. The prescription, design, and fabrication of a successful personal support system is a highly subjective process. The process requires multi-disciplinary clinical effort and involves long delays between initial patient contact and the final delivery of the support system. At least partially responsible for this imprecision is a lack of documented clinical knowledge, objective seat design criteria, and reliable instrumentation for quantitative observation.

Research and development work in wheelchair technology has been concentrated on transport aspects of the wheelchair mobility. Much less effort has been directed to quantifying sitting quality of the user. This sitting quality involves pressure, support, stability, comfort, and function. Due to its subjective nature, sitting quality is difficult to quantify. In recent years, however, efforts have been made towards the development of quantitative assessment in this area A key requirement for continued advancement in the study of finding optimal personal support systems, and the processes of fabricating such systems on an individualized prescription basis is a means for obtaining individualized data on a patient, and arriving at an optimal pressure distribution for that person. A means and method for promptly fabricating a suitable personal support system to accomplish such a personalized seating arrangement is also necessary.

The present invention contemplates a new and improved system for achieving a personalized support system which overcomes all of the above referred problems, and others, and provides a system for arriving at such a support system efficiently, economically, and with improved accuracy.

SUMMARY OF THE INVENTION

In accordance with the present invention there is provided a surface adapted for deforming in accordance with an associated object placed in force contact therewith. A sensor means generates a distribution signal representative of a force distribution along the surface. The deformation of the surface resultant from the associated object is selectively variable to redistribute forces along the surface. A sensor means generates a signal indicative of the force distribution of the object along the surface both initially, and after modifying the deformation.

In accordance with a more limited aspect of the invention, a signal indicative of the contour of the surface is generated. This signal is made available for automated manufacturing of a suitable cushion to facilitate the selected force distribution.

In accordance with another aspect of the present invention, a method is provided for obtaining an optimal surface configuration for obtaining a surface with desired force distribution characteristics.

An advantage of the present invention is the provision of a system whereby an optimal surface formation may be achieved for distribution of forces.

Another advantage of the present invention is the provision of a means for fabricating an accurate surface in accordance with data acquired of a selected surface configuration.

Yet another advantage of the present invention is the provision of means by which an optimal surface for selected force distribution of a patient thereon may be fabricated quickly and inexpensively.

Further advantages will become apparent to one of ordinary skill in the art upon reading and understanding of the subject specification.

BRIEF DESCRIPTION OF THE DRAWINGS

The present invention may take physical form in certain parts and arrangements of parts, preferred embodiments of which will be described in detail in this specification and illustrated in the accompanying drawings which form a part hereof, and wherein.

DETAILED DESCRIPTION OF THE PREFERRED EMBODIMENTS

Figure 1:
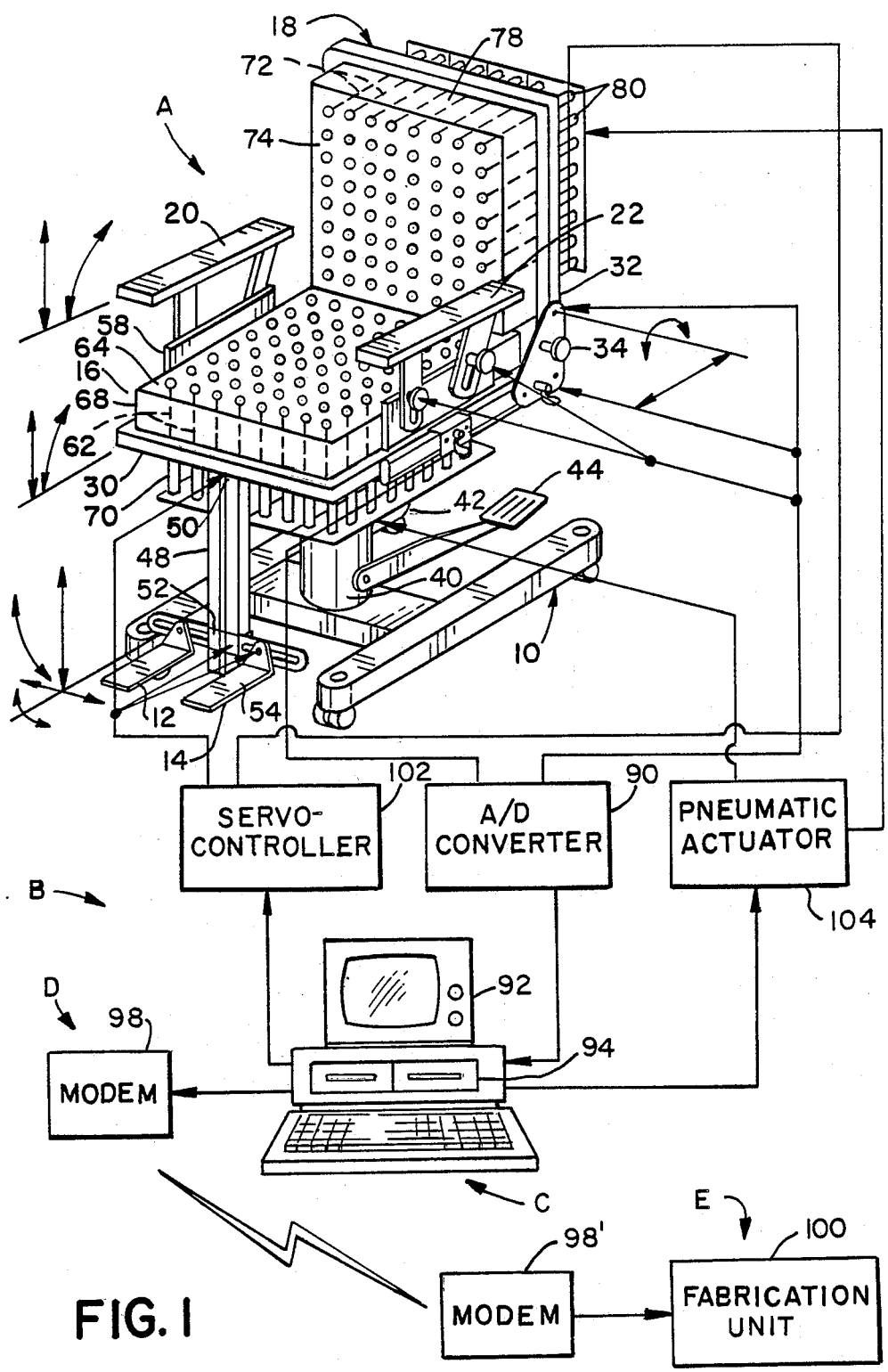
FIG. 1 is a schematic representation of a prescription wheelchair seat system of the present invention.

Turning to FIG. 1, a fitting seat A communicates through interface B with a computer means C. Data generated from the computer means C is passed through communications means D to a fabrication unit E.

The adjustable fitting seat A has four support components plus an electronic measuring system. The supports include the frame 10, foot rest 12, 14, a seat portion 16, and a back portion 18. Additional support may be had from right and left arms rests 20, 22.

The various support structures are each adapted with several degrees of freedom of motion for adjustment in accordance with determining a desirable orientation of the patient which will facilitate desirable posture and/or force distribution of a seated patient.

A horizontal support 30 has mounted along a surface thereof the seat portion 16. The horizontal support 30 also supports a vertical support member 32 which is mounted in reciprocable relationship therewith as illustrated. The back portion 18 is pivotally mounted, at pivot point 34, with the vertical support member 32 so as to be pivotally adjustable therewith as illustrated.

Pivotally connected to the horizontal support 30 is a vertical strut 40 which forms a portion of frame 10. With the illustrated interconnection between horizontal support 30 and vertical strut 40, a relative angular displacement of horizontal support 30 to frame 10 may be made. The frame 10 includes a safety stop 42 to limit the displacement of horizontal support 30.

A foot pedal 44 provides selectable vertical displacement of the horizontal support 30 with respect to the frame 10.

A foot rest support bar or bars 48 is pivotally mounted with the horizontal support 30 at pivot point 50. The foot rest support 48 has, reciprocally mounted thereon, the foot rest 12. Discussion will be made herein only with regard to right foot rest 12. It will be understood, however, that similar structure will be present in the left foot rest 14.

The foot rest 12 is reciprocally mounted to the support bar 50 by slider assembly 52. Pivotally mounted to the slider assembly 52 is foot plate 54.

Turning to the top portion of the Figure, a generally planar side panel 58 is rigidly mounted generally perpendicular to the horizontal support 30. Mounted therewith to afford the degrees of freedom illustrated are the right and left arm rests 20, 22.

With the relative connections and mountings illustrated by the Figure, the following angles and orientations of the fitting seat A may be made. These include: seat height (by adjustment of the horizontal support 30 in relation to the frame 10); seat angle (by adjustment of the angle of horizontal support 30 in relation to the frame 10); back angle (by angular displacement of rear support 34); seat depth (by displacement of the vertical support member 32 in relation to the horizontal support 30); leg angle (by varying the relative position of foot rest support bar or bars 50 in relation to horizontal support 30); leg length (by varying the relative position of slider assembly 52 along foot rest support bar 50); foot angle (by varying relative position of foot plate 54 to slider assembly 52); and forearm angle and elbow height (by varying the relative position of left and right arm rests 20, 22 to side panel 58, and accordingly in relation to horizontal support 30).

All adjustments to angles and relative positioning of the members of fittings seat A may be facilitated by manual adjustment mechanisms as will be easily understood to one of ordinary skill in the art. The preferred embodiment includes means for having these adjustments made by power driven mechanisms. This may be accomplished by implementation electric motors with appropriate gearing, hydraulic motors, or the like as is well understood in the art. Implementation of power driven mechanisms facilitates an easily implemented close loop feedback system.

The seat portion 16 is comprised of a plurality of force and position sensitive transducers 62 which are adapted for giving a signal which is a function of displacement along a longitudinal axis of the transducer. The transducers 62 are in force contact with a seat surface means 64, which is deformable. Deformation of the surface means 64 causes relative longitudinal deformation of a force and position sensitive transducer or transducers which are in a particular area of deformation. In the preferred embodiment, the transducers 62 are spring biased by means such as a foam pad 68 such that deformation of the surface means is functionally related to a magnitude of a force contact therewith. The seat surface means 64 may be comprised of one surface of the foam pad 68.

A series of linearally positionable actuators 70 are connected to the force and position sensitive transducers 62 in a one to one relation. The linear actuators are selectively positionable along their respective axes so as to govern deformation of the seat surface means 64. In this fashion, force of an associated object such as a patient in force contact with the seat surface means 64 may be selectively redistributed by relative placement of a linear actuators 72. A continuously updated distribution signal is available from each of the force and position sensitive transducers 62. An initial curvature may be suitably imparted to the seat surface means 64, though such is not mandatory. Such a curvature functions to provide an initial position which is generally more desirable for the general patient, as well as functioning to orient the patient in a preferred position along the surface 64.

The back portion 18 is, analogous to the seat portion 16, comprised of a series of force and position sensitive transducers in contact with a back portion surface means 74, which, as illustrated, is similarly imparted with an initial angle. Each of the force and position sensitive transducers 72' is engaged longitudinally with a linear actuator 80. With such a construction, relative force and position by placement of the back portion 18 may be measured and redistributed analogously to that of the seat portion 16.

In the preferred embodiment, both the seat portion 16 and the back portion 18 are comprised of 64 actuator/transducer assemblies, suitably arranged in an 8×8 or larger matrix. Implementation of such a mount is found to be adequate for suitable accuracy in measurement of force and shape distribution and redistribution thereof.

Signals from each of the force and position sensitive transducers are fed to an analog to digital (A/D) convertor 90. It will be appreciated, however, when suitable, digital transducers are implemented, the A/D convertor 90 is not necessary. The A/D convertor 90 creates suitable digital information about the relative force measured on each force and position sensitive transducer 62, 72. This digital information is passed to the computer means C for processing and analysis. An image of the force and shape distribution is displayable on display means 92. The digital information may also be stored on a tangible media such as a disc written in disc drive 94, or it may alternatively be sent to a printer or the like.

The digital information is also suitably modulated by means such as modem 98, wherefrom it may be received by a corresponding modem 98' for use in remote analysis or fabrication of a suitable seating assembly by a fabrication unit illustrated at 100. The computer means C also transmits digitally encoded information to servo controller 102 which selectively governs powered positioning of the various orientations of the fitting seat A, as well as pneumatic actuator 104 which facilitates redistribution of various forces of the associated object of patient along the surface means 64, 74.

Figure 2:
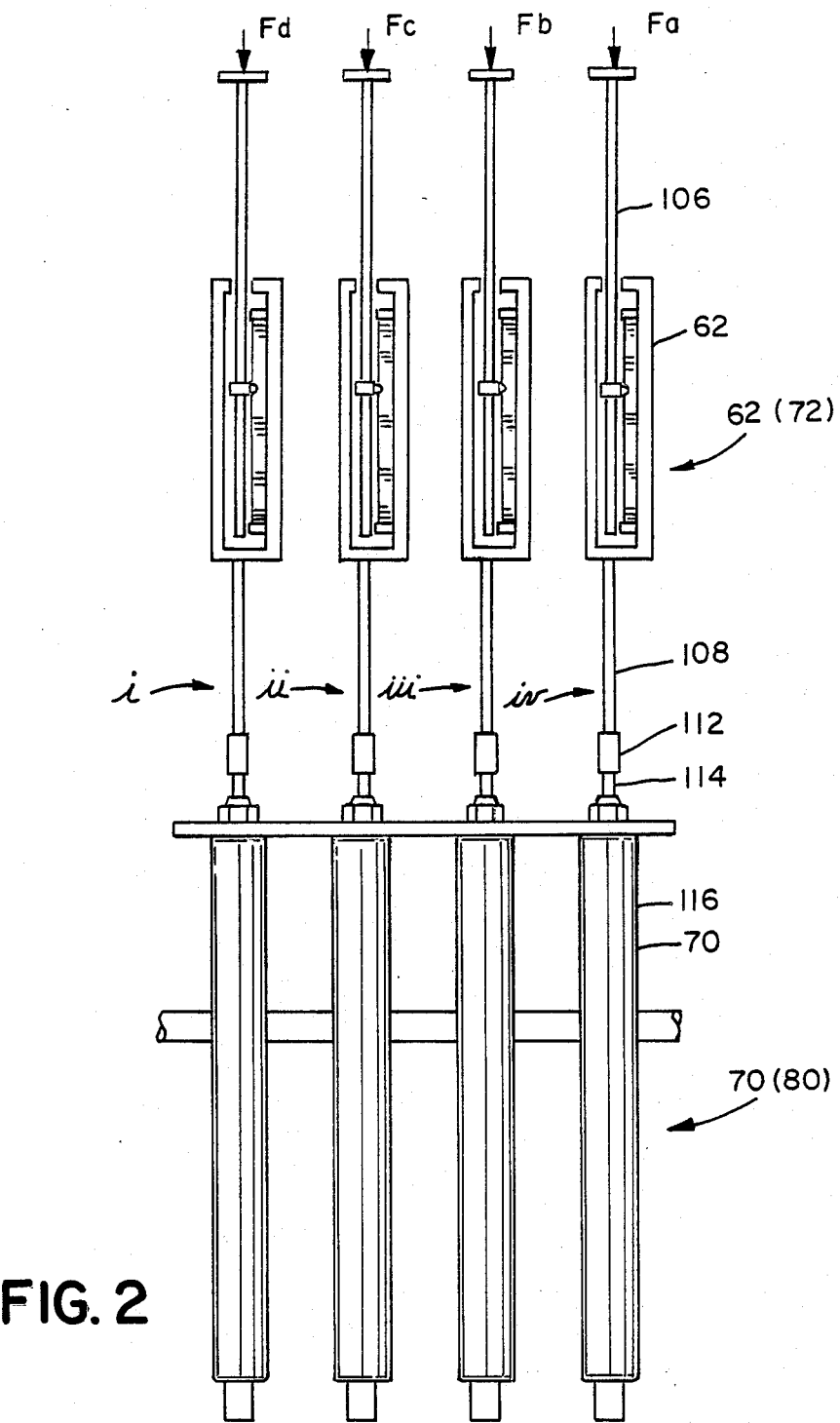
FIG. 2 is a cross-sectional view of a portion of a transducer/actuator array of the system of FIG. 1.

Turning now to FIG. 2, a detailed description of the transducer/actuator assembly of the seat portion 16 and the back portion 18 of the fitting seat A will be described. Illustrated in the Figure are four of the transducer/actuator assembles (i-iv) of both the seat portion 16 and the back rest 18. Each of the force and position sensitive transducers is illustrated as a piston-like slide assembly which is spring-biased or the like each of which is mounted in series as shown or alternatively in parallel.

Longitudinal pressure on rod member 106 of each of the assemblies causes proportional longitudinal displacement of the rod member 106 in relation to a corresponding connection rod member 108. It will therefore be seen that the spring biasing of each linear actuator 62 operates in conjunction with the spring biasing resultant from the foam pads 68 (FIG. 1) to facilitate a net longitudinal displacement of rod member 106 which is directly proportional to amount of force F on its respective rod member 106. Alternatively, spring biasing may be accomplished by use of conventional springs on each of the transducers 106.

Each connecting rod 108 is attached through coupling 112 to a piston 114 of each linear actuator 70 (80). The extension of the piston 114 in relation to its cylinder 116 may be varied by selection of the pneumatic actuator 104 (FIG. 1).

Turning back to FIG. 1, with continuing reference to FIG. 2, the process by which a selected force distribution for a prescription seating arrangement may be achieved will be described. A patient is seated on the fitting seat A. The seat height, seat angle, back angle, seat depth, leg angle, leg length, foot angle, forearm angle, and elbow angle are set to an initial position. A spring bias is resultant from the foam pads 68, 78 in conjunction with each of the force and position sensitive transducers 62, 72. When the patient is seated, deflections of rod members 106 (FIG. 2) occur in proportion to the force placed longitudinally therealong. A corresponding signal will be generated by each linear transducer 62, 72, which is illustrated as a linear potentiometer, the resistance of which is directly proportional to its linear displacement. Signals are passed from the linear transducers 62, 72, through A/D convertor 90 from which a digital signal indicative of displacement is fed into computer means C.

Accordingly, contour data is generated and passed to computer means C which is adapted to form a visual image of the force distribution along a surface area on display means 92. At this point, the contour data is viewable by a physician or technician. Should it be determined that an optimal force distribution is not present, such as when a certain portion of a person is receiving a disproportionate amount of force from the chair, or if it is determined that corrective forces need be applied to certain portions of the patient's anatomy, the physician or technician may select appropriate redistribution. This may be accomplished manually or alternatively through computer means C. In the latter situation, digitized data is passed through servo controller 102 to facilitate automated chair positioning. In either instance, and appropriate longitudinal changes of pistons of selected linear actuators 70, 80 are facilitated by digital control of pneumatic actuator 104.

It will be seen that forces may be redistributed to neighboring portions of a patient by deflection or reformation of the surface means by selective control of various of the pneumatic pistons. After each such selection, or continuously thereduring, updated force distribution data is acquired from the linear transducers and passed through to computer means C. Eventually, a satisfactory distribution is acquired by continuation of this process. As noted above, this digitized data may be stored or modulated and transmitted to a remote unit from which fabrication may occur.

Figure 3:
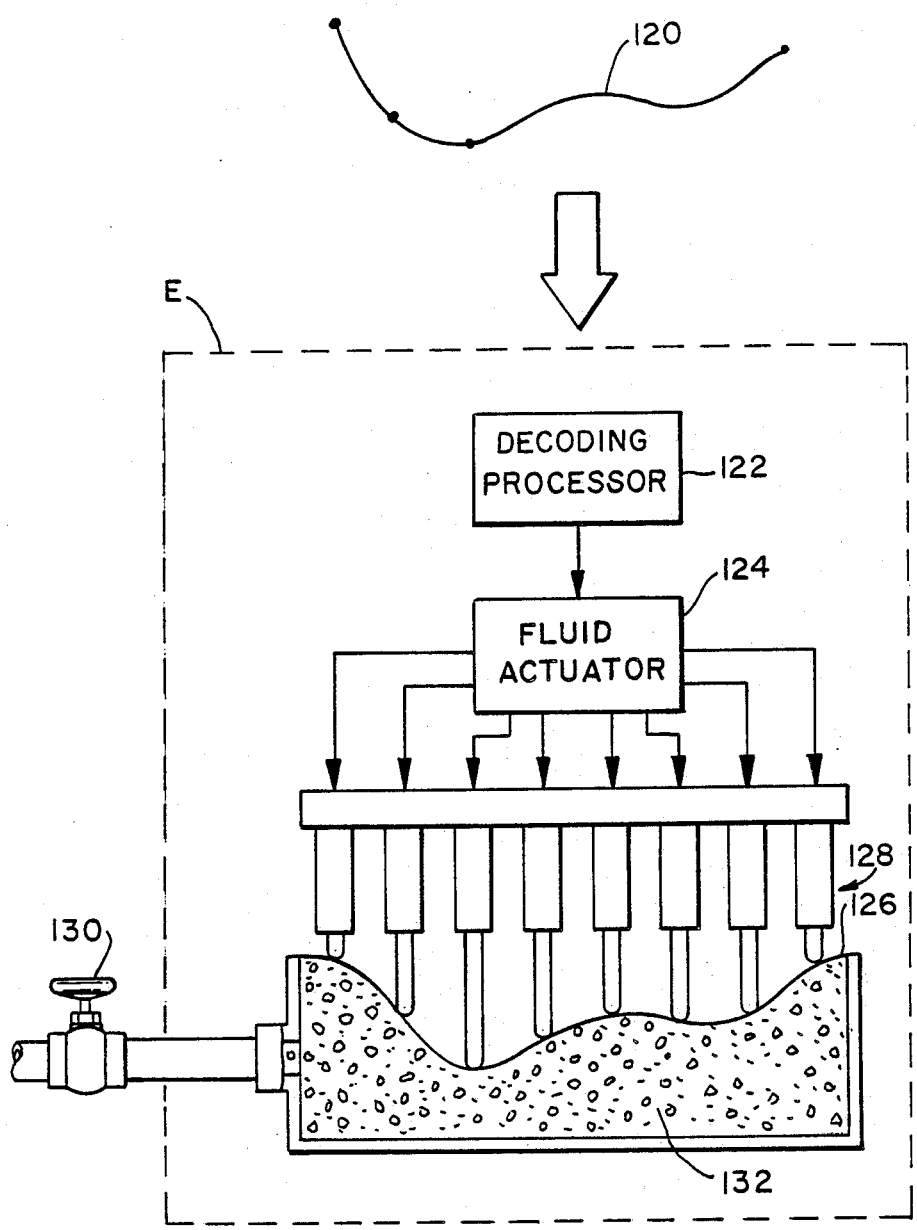
FIG. 3 is a cross-sectional view of suitable fabrication unit for fabrication of a surface in conjunction with data generated from the system of FIG. 1.

Turning now to FIG. 3, one means by which contour data may be used to fabricate a suitable seat cushion is presented. Contour data 120 is graphically illustrated in two dimensions, although it will be appreciated that three-dimensional data is ideally represented thereby. The scale may be displacement versus force, or may be logically manipulated to already be indicative of desired seat contour. At a fabricating unit E, this data is decoded by a decoding processor 122. In the illustrated example of FIG. 3, the decoding processor drives a fluid, such as a fluid actuator 124 which works on a series of pistons 128 to deflect a deformable membrane 126 in accordance with a desired cushion configuration. A valve 130 is open, and liquified foam material is injected into a cavity 132 formed in part by the membrane 126. The valve is closed, and the injected foam permitted to harden to form a seat cushion with desired characteristics.

When constructing in this fashion, a seat cushion may be constructed with a desirable curvature within an extremely short time period for arriving at a prescription for the patient. By implementation of a modern interconnection, such as that 98 of FIG. 1 such fabrication may be carried out remotely at a fabrication center.

The invention has been described with reference to the preferred embodiments, obviously, modifications and alterations will occur to others upon the reading and understanding of this specification. It is intended to include all such modifications and alterations insofar as they come within the scope of the appended claims or the equivalents thereof.

What is claimed is:

1. A selective force distribution system comprising:
a surface means adapted for deforming in accordance with an associated object placed in force contact therewith;
sensor means for generating a distribution signal representative of a force distribution along the surface means;
deformation means for selectively varying deformation of the surface means; and
the sensor means further including means for generating an updated distribution signal representative of a modified force distribution along the surface means incurred as a result of a varied deformation thereof.

2. The system of claim 1 further comprising means for generating a contour signal representative of a contour of the surface means.

3. The system of claim 2 further comprising means for controlling the deformation means in accordance with a selected deformation signal.

4. The system of claim 3 wherein the sensor means includes an array of force and position sensitive transducers.

5. The system of claim 4 wherein the deformation means includes a plurality of linearly positionable actuators.

6. The system of claim 5 further comprising biasing means operatively connected to the surface means for controlling deformation of the surface means in accordance with the associated object placed in force contact therewith, such that deformation is functionally related to a magnitude of the force contact of the associated object.

7. The system of claim 6 further comprising processor means for generating the contour signal and means for generating a visual representation of one of the force distributions 8. The system of claim 7 further comprising means for fabricating a manufactured surface in accordance with the contour signal.

9. A method of defining a surface having a contour for placing an associated object in force contact therewith in a selected force distribution in relation to the surface, comprising the steps of:
    deforming a surface in accordance with an associated object placed in force contact therewith;
    generating a distribution signal representative of a force distribution along the surface means;
    selectively varying deformation of the surface; and
    generating an updated distribution signal representative of a modified force distribution along the surface incurred as a result of a varied deformation thereof 10. The method of claim 9 further comprising the step of generating a contour signal representative of a contour of the surface.

11. The method of claim 10 further comprising the step of controlling deformation of the surface.

12. The method of claim 11 further comprising the step of generating a deformation signal for selectively controlling deformation of the surface.

13. The method of claim 11 further comprising the step of generating a visual representation of one of the force distributions.

14. The system of claim 12 further comprising the step of fabricating a manufactured surface in accordance with the contour signal.

15. A computer aided wheelchair prescription system comprising:
    a seat portion including an array of pressure sensitive transducers on a surface thereof;
    deformation means for selectively varying a contour of the surface; and
    means for generating a distribution signal representative of a force distribution of an associated object in force contact with the surface.

16. The wheelchair prescription system of claim 15 further comprising means for generating a contour signal indicative of the contour of the surface.

17. The wheelchair prescription system of claim 16 wherein the seat portion further includes a bottom seat portion and a back seat portion, and the surface includes a bottom surface portion associated with the bottom seat portion and a back surface portion associated with the back seat portion.

18. The wheelchair prescription system of claim 17 further comprising means for controlling operation of the deformation means in accordance with a deformation signal, and means for generating a deformation signal in accordance with a preselected force distribution of the associated object against the surface.

19. The wheelchair prescription system of claim 18 further comprising means adapted for transmitting the contour signal to an associated fabrication unit.

20. The wheelchair prescription system of claim 18 further comprising means for selectively varying an orientation of the surface means with respect to vertical.

* * * * *